US009398762B2

(12) United States Patent
Auerbach et al.

(10) Patent No.: US 9,398,762 B2
(45) Date of Patent: *Jul. 26, 2016

(54) PRODUCTION OF FERTILE XY FEMALE ANIMALS FROM XY ES CELLS

(71) Applicant: Regeneron Pharmaceuticals, Inc., Tarrytown, NY (US)

(72) Inventors: Wojtek Auerbach, Ridgewood, NJ (US); Thomas DeChiara, Rye Brook, NY (US); William Poueymirou, White Plains, NY (US); David Frendewey, New York, NY (US); David Valenzuela, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 72 days.

This patent is subject to a terminal disclaimer.

(21) Appl. No.: 14/538,209

(22) Filed: Nov. 11, 2014

(65) Prior Publication Data

US 2015/0067901 A1    Mar. 5, 2015

Related U.S. Application Data

(63) Continuation of application No. 13/157,728, filed on Jun. 10, 2011, now Pat. No. 9,149,026.

(60) Provisional application No. 61/353,896, filed on Jun. 11, 2010.

(51) Int. Cl.
| *A01K 67/027* | (2006.01) |
| *C12N 5/0735* | (2010.01) |
| *C12N 9/02* | (2006.01) |
| *C12N 15/873* | (2010.01) |

(52) U.S. Cl.
CPC .......... *A01K 67/0276* (2013.01); *C12N 5/0606* (2013.01); *C12N 9/0091* (2013.01); *C12N 15/873* (2013.01); *A01K 2207/12* (2013.01); *A01K 2217/054* (2013.01); *A01K 2227/105* (2013.01); *A01K 2267/0331* (2013.01); *C12N 2500/60* (2013.01); *C12N 2517/10* (2013.01)

(58) Field of Classification Search
CPC ............. C12N 2517/10; C12N 15/873; C12N 2500/60; C12N 5/0606; C12N 9/0091; A01K 2267/0331; A01K 67/0276; A01K 2217/054; A01K 2227/105; A01K 2207/12
See application file for complete search history.

(56) References Cited

U.S. PATENT DOCUMENTS

| 7,294,754 B2 | 11/2007 | Poueymirou et al. |
| 7,576,259 B2 | 8/2009 | Poueymirou et al. |
| 7,659,442 B2 | 2/2010 | Poueymirou et al. |
| 9,149,026 B2 | 10/2015 | Auerbach et al. |
| 2003/0204862 A1 | 10/2003 | Kuehn et al. |
| 2005/0216966 A1 | 9/2005 | Nagao |
| 2007/0155013 A1 | 7/2007 | Akaike et al. |
| 2007/0245424 A1 | 10/2007 | Nagao |
| 2008/0124801 A1 | 5/2008 | Mee et al. |
| 2011/0307968 A1 | 12/2011 | Auerbach et al. |
| 2015/0376651 A1 | 12/2015 | Frendewey et al. |
| 2016/0046960 A1 | 2/2016 | Frendewey et al. |

FOREIGN PATENT DOCUMENTS

| CN | 1423522 A | 6/2003 |
| CN | 1217746 A | 5/2005 |
| CN | 1649489 A | 8/2005 |
| CN | 101506354 A | 8/2009 |
| EP | 1516924 A1 | 3/2005 |
| WO | WO 97/41209 | 11/1997 |
| WO | WO 01/45500 A1 | 6/2001 |
| WO | WO 2008/007704 A1 | 2/2008 |
| WO | WO 2011/044684 A1 | 4/2011 |
| WO | WO 2011/156723 A1 | 12/2011 |
| WO | WO 2015/200805 A2 | 12/2015 |

OTHER PUBLICATIONS

Affara, "The role of the Y chromosome in male infertility," Expert Rev. Mol. Med., vol. 2001, pp. 1-16, 2001.
Alton et al., "The behavior of the X- and Y-chromosomes in the oocyte during meiotic prophase in the B6.Y(TIR) sex-reversed mouse ovary," Reproduction, vol. 135(2), pp. 241-252, 2008.
Certificate of Analysis for KNOCKOUT™ DMEM, Life Technologies, Catalog No. 10829, Lot No. 1677060, May 21, 2015.
D'Aiuto et al., "Large-scale generation of human iPSC-derived neural stem cells/early neural progenitor cells and their neuronal differentiation," Organogenesis, vol. 10(4), pp. 365-377, Oct. 2, 2014.
Fan et al., "107 Genetic Inactivation of the Sry Gene in Argali Wild and Romney Domestic Sheep with CRISPR/Cas Systems for Producing Sex-Reversed Female Animals," Reproduction Fertility and Development, vol. 26(1), p. 167, Dec. 5, 2013.
Frendewey ,"VelociGene: Large-scale Modification of Rodent Genomes," Wellcome Trust Advanced Course: Genetic Engineering of Mammalian Stem Cells, Mar. 13, 2014.
Frendewey, "VelociGene: Large-scale Modification of Rodent Genomes," Wellcome Trust Advanced Course: Genetic Engineering of Mammalian Stem Cells, Feb. 20, 2015.
Hirano et al., "Human and Mouse Induced Pluripotent Stem Cells Are Differentially Reprogrammed in Response to Kinase Inhibitors," Stem Cells and Development, vol. 21(8), pp. 1287-1298, May 20, 2012.
Kashimada et al., "Sry: the master switch in mammalian sex determination," Development, vol. 137(23), pp. 3921-3930, Dec. 2, 2010.

(Continued)

*Primary Examiner* — Thaian N Ton
(74) *Attorney, Agent, or Firm* — Yong-Jin Choi; Alston & Bird LLP

(57) ABSTRACT

Methods and compositions are described for making phenotypically female fertile animals from XY donor cells and suitable host embryos. Culture media and methods are provided for maintaining XY donor cells in culture that after introduction into a host embryo and gestation in a suitable host will result in fertile XY female animals. Methods and compositions are described for making fertile female animals in an F0 generation from a donor XY cell and a host embryo, as are methods for making F1 progeny that are homozygous for a modification from a heterozygous F0 fertile male and a heterozygous F0 fertile female sibling.

21 Claims, 2 Drawing Sheets

(56) References Cited

OTHER PUBLICATIONS

Kato et al., "Production of Sry knockout mouse using TALEN via oocyte injection," Scientific Reports, vol. 3, p. 3136, 2013 (published Nov. 5, 2013).
Kuno et al., "Generation of fertile and fecund F0 XY female mice from XY ES cells," Transgenic Research, vol. 24(1), pp. 19-29, 2014 (epub Aug. 3, 2014).
Mazeyrat et al., "The mouse Y chromosome interval necessary for spermatogonial proliferation is gene dense with syntenic homology to the human AZFa region," Hum. Mol. Genet., vol. 7(11), pp. 1713-1724, 1998.
PCT/US2015/038001 Invitation of Pay Additional Fees mailed Nov. 13, 2015.
Sargent et al., "The critical region of overlap defining the AZFa male infertility interval of proximal Yq contains three transcribed sequences," J. Med. Genet., vol. 36(9), pp. 670-677, 1999.
Turner, "Meiotic sex chromosome inactivation," Development vol. 134(1), pp. 1823-1831, 2007.
U.S. Appl. No. 13/157,728, Notice of Allowance mailed May 27, 2015.
U.S. Appl. No. 14/926,773, Requirement for Restriction/Election mailed Feb. 16, 2016.
Wang et al., "TALEN-mediated editing of the mouse Y chromosome," Nature Biotechnology, vol. 31(6), p. 530-532, 2013 (epub May 12, 2013).
Wen et al., "Completely ES Cell-Derived Mice Produced by Tetraploid Complementation Using Inner Cell Mass (ICM) Deficient Blastocysts," PLoS One, vol. 9(4), e94730, Apr. 14, 2014.
U.S. Appl. No. 13/157,728 Non-Final Office Action mailed Dec. 15, 2014.
Chung, et al., "Human Embryonic Stem Cell Lines Generated without Embryo Destruction", Cell Stem Cell 2, pp. 113-117 (Feb. 2008).
Bernart, et al., "Frozen storage of Ham's F-10 medium for human in-vitro fertilization," Human Reproduction, 5:610-612 (1990).
Bronson et al., "High incidence of XXY and XYY males among the offspreing of female chimeras from embryonic cells," Proc. Natl. Acad. Sci. USA, Apr. 1995, vol. 92:3120-3123.
Chen, W., et al., "Formation of germline chimeras from murine embryonic stem cell lines," 1999, Acta Genetica Sinica, 26(2): 126-134 English Abstract.
Cheng, et al., "Improved generation of C57BL/6J mouse embryonic stem cells in a defined serum-free media," Genesis, Jun. 2004, vol. 39(2):100-104.
Colvin et al., "Male-to-Female Sex Reversal in Mice Lacking Fibroblast Growth Factor 9," Cell, Mar. 23, 2001, vol. 104:875-889.
Dechiara, T.M., et al., "VelociMouse: Fully ES Cell-Derived F0-Generation Mice Obtained from the Injection of ES Cells into Eight-Cell-Stage Embryos," Jan. 1, 2009, Methods in Molecular Biology, 530(16): 311-324.
Dulbecco, et al., "Plaque production by the polyoma virus," Virology, vol. 8(3):396-7 (Jul. 1959).
Hoekstra et al., Multiple origins of XY female mice (genus Akodon): phylogenetic and chromosomal evidence,: Proc. R. Soc. Lond. B, Sep. 22, 2000, vol. 267(1455):1825-31.
International Search Report of International Application No. PCT/US2011/039997, mailed Sep. 6, 2011.
Kallos, et al., "Inoculation and Growth Conditions for High-Cell-Density Expansion of mannalian Neural Stem Cells in Suspension Bioreactors," Bioengineering, 63:473-483 (1999).
Li, et al., "Non-equivalence of cloned and clonal mice, Current Biology," R756-R757, vol. 15, No. 18 (Sep. 19, 2005).
Lovell-Badge et al., "XY female mice resulting froma heritable mutation in the primary testis-determining Tdy," Development, Jul. 1, 1990, vol. 109:635-646.
PCT/US2011/039997 International Preliminary Report on Patentability and Written Opinion mailed Dec. 14, 2012.
Porkka, et al., "Cloning and Characterization of a Novel Six-Transmembrane Protein STEAP2, Expressed in Normal and Malignant Prostate," Lab. Invest., 82:1573-1582 (2002).
Poueymirou et al., "F0 generation mice fully derived from gene-targeted embryonic stem cells allowing immediate analysis," Nature Biotechnology, Epub Dec. 24, 2006, vol. 25(1):91-99.
Song, Z., et al., "Formation of Mouse Chimeras from Early Embryonic Pluripotential Stein Cell," 1993, Acta Genetica Sinica, 20(6): 499-503 English Abstract.
Tang, et al., "A mouse knockout library for secreted and transmembrane proteins," Nature Biotechnology, 28:749-755 (2010).
Tong, Y., et al., "Establishment of a High Germline Competent CS7BL I 6J ES Cell Line," 1999, Acta Genetica Sinica, 26(5): 468-473 English Abstract.
U.S. Appl. No. 13/157,728 Advisory mailed Apr. 30, 2013.
U.S. Appl. No. 13/157,728 Final Rejection mailed Nov. 16, 2013.
U.S. Appl. No. 13/157,728 Non-Final Rejection mailed Jul. 11, 2012.
Ward et al., "The 5T4 oncofoetal antigen is an early differentiation marker of mouse ES cells and its absence is a means to assess pluripotency," The Journal of Cell Science, vol. 116:4533-4542 (Nov. 15, 2003).

Fertility Analysis of Phenotypically Female F0 Generation Mice Derived from XY ES Cell Clones

| Clone | Genotype | F0s Set Up to Breed (#) | F0s with Litters (#) | F0s with Litters (%) | Litters (#) | Total Pups (#) | Pups Per Litter (#) |
|---|---|---|---|---|---|---|---|
| 860a-H1 | XY | 2 | 1 | 50 | 3 | 11 | 3.7 |
| 829a-E2 | XY | 1 | 0 | 0 | 0 | 0 | --- |
| 5339a-A5 | XY | 2 | 2 | 100 | 8 | 55 | 6.9 |
| 5315a-D1 | XY | 1 | 1 | 100 | 8 | 48 | 6 |
| 5311b-D1 | XY | 4 | 1 | 25 | 4 | 37 | 9.3 |
| 5310a-D4 | XY | 1 | 1 | 100 | 6 | 32 | 5.3 |
| 5310a-B1 | XY | 6 | 6 | 100 | 34 | 188 | 5.5 |
| 5310a-A5 | XY | 2 | 2 | 100 | 11 | 75 | 6.8 |
| 5137b-E1 | XY | 2 | 2 | 100 | 12 | 74 | 6.2 |
| 294d-A5 | XY | 1 | 0 | 0 | 0 | 0 | --- |
| 1553a-A10 | XY | 2 | 0 | 0 | 0 | 0 | --- |
| 1533b-A2 | XY | 2 | 1 | 50 | 2 | 16 | 8 |
| 13304a-D5 | XY | 1 | 1 | 100 | 2 | 15 | 7.5 |
| 1313h-F3 | XY | 2 | 1 | 50 | 1 | 2 | 2 |
| 12221b-B3 | XY | 1 | 1 | 100 | 1 | 10 | 10 |
| 11465d-G1 | XY | 1 | 1 | 100 | 6 | 49 | 8.2 |
| 884a-D1 | XY | 2 | 0 | 0 | 0 | 0 | --- |
| Summary | | 33 (Σ) | 21 (Σ) | 63% | 98 (Σ) | 592 (Σ) | 6 (avg) |

| | | Effect of DMEM and Low-Salt DMEM on Formation of XY Females in the F0 Generation from XY ES Cells | | | | | |
|---|---|---|---|---|---|---|---|
| | ES Clone | Media | Embryos Transferred (#) | Pups Born (#) | Male VM (#) | Female VM (#) | XY Genotyping |
| | | Clone Production & Thawing | | | | | |
| 1 | d-G4 | Low-salt DMEM | 50 | 19 | 8 | 4 | all females are XY |
| 2 | d-A1 | Low-salt DMEM | 50 | 5 | 0 | 0 | all females are XY |
| 3 | e-C2 | Low-salt DMEM | 50 | 4 | 3 | 1 | all females are XY |
| 4 | e-D1 | Low-salt DMEM | 50 | 22 | 12 | 2 | all females are XY |
| 5 | e-H2 | Low-salt DMEM | 50 | 14 | 10 | 0 | --- |
| 6 | e-H3 | Low-salt DMEM | 50 | 11 | 6 | 0 | --- |
| | | Totals | 300 | 75 | 39 | 7 | all females are XY |
| 8 | d-C6 | Low-salt DMEM + 10% FS | 50 | 14 | 2 | 5 | all females are XY |
| 9 | d-A5 | Low-salt DMEM + 10% FS | 50 | 26 | 7 | 7 | all females are XY |
| 10 | e-B6 | Low-salt DMEM + 10% FS | 50 | 18 | 8 | 5 | all females are XY |
| 11 | e-A5 | Low-salt DMEM + 10% FS | 50 | 18 | 13 | 3 | all females are XY |
| 12 | e-C6 | Low-salt DMEM + 10% FS | 50 | 19 | 11 | 3 | --- |
| 13 | e-F5 | Low-salt DMEM + 10% FS | 50 | 19 | 13 | 5 | --- |
| | | Totals | 300 | 114 | 54 | 28 | all females are XY |
| 15 | d-H9 | Low-salt DMEM +NaCl+NaHCO$_3$ | 50 | 30 | 9 | 0 | --- |
| 16 | d-C10 | Low-salt DMEM +NaCl+NaHCO$_3$ | 50 | 14 | 4 | 0 | --- |
| 17 | e-A9 | Low-salt DMEM +NaCl+NaHCO$_3$ | 50 | 3 | 0 | 0 | --- |
| 18 | e-G8 | Low-salt DMEM +NaCl+NaHCO$_3$ | 50 | 22 | 3 | 0 | --- |
| 19 | e-H9 | Low-salt DMEM +NaCl+NaHCO$_3$ | 50 | 2 | 0 | 0 | --- |
| | | Totals | 250 | 71 | 16 | 0 | --- |

PRODUCTION OF FERTILE XY FEMALE ANIMALS FROM XY ES CELLS

CROSS-REFERENCE TO RELATED APPLICATIONS

This application is a continuation application of U.S. application Ser. No. 13/157,728, filed on Jun. 10, 2011, which claims the benefit of U.S. Provisional Patent Application No. 61/353,896, filed on Jun. 11, 2010.

FIELD

The invention relates to the manufacture of fertile female animals derived from XY embryonic stem ("ES") cells and having a XY karyotype. In a particular embodiment, methods and compositions for making fertile XY female mice from XY donor murine ES cells are described. In vitro fertilization methods for favoring the formation of phenotypic females are also described.

BACKGROUND

Nearly all commonly employed ES cell lines for making genetically modified mice are genotypic male (XY) ES cell lines. As a result, in the F0 generation, all XY animals are male. Most genetic modifications are carried out by targeting the XY ES cells to create a modification of one of two existing alleles, i.e., the donor mouse ES cell is heterozygous for the genetic modification. However, it is often desirable to obtain a mouse that is homozygous for the genetic modification. Because essentially no fully ES cell-derived female mice are born in the F0 generation that comprise the modification, the F0 male is typically bred to a female (e.g., a matched inbred female) to generate a litter in which at least one female (an F1 female) might be heterozygous for the genetic modification. The heterozygous F1 female is then intercrossed with an F1 heterozygous male, to obtain a homozygous progeny. Such breeding requirements represent costly and time-consuming steps. It is desirable to generate a breeding pair in an F0 generation, or at least to generate an F0 female that is largely or fully derived from the donor (XY male) ES cell.

There is a need in the art for methods and compositions for making a fertile female animal in the F0 generation from a donor male (XY) ES cell and a host embryo.

SUMMARY

In one aspect, a method for making a fertile female nonhuman animal from an XY donor cell is provided, comprising: (a) introducing a nonhuman XY donor cell into a nonhuman host embryo to form a chimeric embryo; and, (b) gestating the chimeric embryo to form a nonhuman female animal, wherein the nonhuman female animal is XY and upon attaining sexual maturity is fertile.

In one embodiment, the nonhuman animal is a mouse.

In one embodiment, the nonhuman XY female animal is formed in the F0 generation. In one embodiment, the nonhuman female XY animal in the F0 generation is a mouse and has a coat color 100% derived from the donor cell. In one embodiment, the nonhuman female XY animal formed in the F0 generation is at least 90%, 92%, 94%, 96%, 98%, or 99.8% derived from the XY donor cell. In one embodiment, the nonhuman female XY animal in the F0 generation is about 100% derived from the donor cell. In one embodiment, the contribution of a host embryo cell to the nonhuman female XY animal in the F0 generation is determined by a quantitative assay that is capable of detecting 1 cell in 2,000 (0.05%), and no tissue of the female XY animal is positive for host embryo cell contribution.

In one embodiment, the donor cell comprises a genetic modification. In one embodiment, the genetic modification comprises a deletion in whole or in part of an endogenous nucleic acid sequence; a substitution of one or more nucleic acids; a replacement of an endogenous nucleic acid sequence, e.g. a gene, in whole or in part with a heterologous nucleic acid sequence; a knockout; and/or, a knock-in.

In one embodiment, the method further comprises a step of breeding an F0 generation XY male heterozygous for the genetic modification with a F0 generation XY female heterozygous for the genetic modification (e.g., a sibling), and obtaining from said breeding an F1 generation animal homozygous for the genetic modification.

In one embodiment, the XY donor cell before introduction into the host embryo is maintained in a medium comprising base medium and supplements, wherein the base medium exhibits a characteristic selected from the group consisting of: (a) an osmolality of about 250-310 mOsm/kg; (b) a conductivity of about 11-13 mS/cm; (c) an alkaline metal and halide salt in a concentration of about 60-105 mM; (d) a carbonic acid salt concentration of about 20-30 mM; (e) a total alkaline metal halide salt and carbonic acid salt concentration of no more than about 85-130 mM; and (f) a combination thereof.

In one embodiment, the supplements comprise components for maintaining ES cells in culture. In one embodiment, the supplements comprise one or more of fetal bovine serum (FBS), glutamine, antibiotic(s), pyruvate, nonessential amino acids, 2-mercaptoethanol, and LIF.

In one embodiment, the base medium is a low-salt DMEM. In a specific embodiment, the low-salt DMEM has an NaCl concentration of 85-130 mM. In one embodiment, the base medium is a low osmolality DMEM. In a specific embodiment, the low osmolality DMEM has an osmolality of 250-310 mOsm/kg. In one embodiment, the base medium is a low conductivity DMEM. In a specific embodiment, the low conductivity DMEM has a conductivity of 11-13 mS/cm.

In one embodiment, the donor cell is maintained in the recited base medium plus supplements before introduction into the host embryo for about 1, 2, 3, 4, 5, 6 days, 1 week, 8, 9, 110, 11, or 12 days, 2 weeks, 3 weeks, or 4 weeks or more. In a specific embodiment, the donor cell is maintained in the base medium plus supplements for at least a week before introduction into the host embryo. In a specific embodiment, the donor cell is maintained in the base medium plus supplements for 2-4 weeks before introduction into the host embryo.

In one embodiment, the host embryo is a 2-cell stage, 4-cell stage, 8-cell stage, 16-cell stage, 32-cell stage, or 64-cell stage embryo. In another embodiment, the host embryo is a blastocyst. In one embodiment, the embryo is in a stage selected from a pre-morula stage, a morula stage, an uncompacted morula stage, and a compacted morula stage. In one embodiment, the embryo stage is selected from a Theiler Stage 1 (TS1), a TS2, a TS3, a TS4, a TS5, and a TS6, with reference to the Theiler stages described in Theiler (1989) "The House Mouse: Atlas of Mouse Development," Springer-Verlag, New York. In a specific embodiment, the Theiler Stage is selected from TS1, TS2, TS3, and a TS4. In one embodiment, the embryo comprises a zona pellucida, and the donor cell is an ES cell that is introduced into the embryo through a hole in the zona pellucida.

In one embodiment, the embryo comprises a pre-blastocyst embryo. In one embodiment, the embryo is a morula-stage embryo. In a specific embodiment, the morula-stage embryo is aggregated. In one embodiment, the embryo is a zona-less embryo.

In one embodiment, the XY donor cell is selected from an ES cell, an induced pluripotent stem (iPS) cell, a pluripotent cell, and a totipotent cell. In a specific embodiment, the XY donor cell is a mouse ES cell and the host embryo is a mouse embryo.

In one embodiment, the XY donor cell is an ES cell from an inbred mouse strain. In one embodiment, the XY donor cell is an ES cell from a hybrid or outbred mouse strain.

In one embodiment, the host embryo is a mouse host embryo. In one embodiment, the mouse host embryo is from an inbred strain, in another embodiment from a hybrid or an outbred strain. In one embodiment, the donor cell is a mouse donor cell. In one embodiment, the host embryo and the donor cell are both mouse, and each is independently selected from a mouse that is a 129 strain, a C57BL/6 strain, a mix of 129 and C57BL/6, a BALB/c strain, or a Swiss Webster strain. In a specific embodiment, the mouse is 50% 129 and 50% C57BL/6. In one embodiment, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836). In one embodiment the mouse is a C57BL strain, in a specific embodiment selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, C57BL/Ola. In a specific embodiment, the mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain.

In one embodiment, the XY female mouse produces 1, 2, 3, 4, 5, 6, 7, 8, or 9 litters of live mice during its lifetime. In one embodiment, the XY female mouse produces at least 1, 2, 3, 4, 5, 6, 7, 8, 9, or 10 pups per litter. In one embodiment, the XY female mouse produces about 4-6 pups per litter. In one embodiment, the XY female mouse produces 2-6 litters, wherein each litter has at least 2, 3, 4, 5, or 6 pups. In one embodiment, about 10%, 15%, 20%, 25%, 30%, 35%, 40%, 45%, or 50% of the pups are XY female pups. In a specific embodiment, about 15%-25% are XY female pups.

In one aspect, a method for making a mouse that is homozygous for a genetic modification is provided, employing an XY ES cell that is heterozygous for the genetic modification. In one embodiment, the method comprises genetically modifying an XY donor ES cell to form a heterozygous XY donor ES cell, maintaining the heterozygous XY donor ES cell in a low salt and/or low osmolality or low contductivity medium, introducing the heterozygous XY donor ES cell into a pre-morula host embryo, gestating the host embryo, after gestation obtaining a fertile F0 generation female XY mouse that comprises the heterozygous modification and is at least in part derived from the donor ES cell, and after gestation obtaining a fertile F0 generation male XY mouse that comprises the heterozygous modification and that is at least in part derived from the donor ES cell, and breeding the F0 male and the F0 female to obtain an F1 progeny that comprises a homozygous modification.

In one embodiment, the F0 generation female XY mouse and/or the F0 generation male XY mouse is at least 20% or more derived from the donor ES cell. In one embodiment, the F0 female XY mouse is at least 30%, 40%, 50%, 60%, 70%, or 80% derived from the donor ES cell.

In one embodiment, the F0 generation female XY mouse and/or the male XY mouse is at least 90% derived from the donor ES cell. In one embodiment, the F0 generation female XY mouse is at least 92%, 94%, 96%, 98%, 99%, or 99.8% derived from the donor ES cell. In one embodiment, the F0 female XY mouse and/or the F0 male XY mouse has a coat color that is 100% derived from the ES cell.

In one embodiment, the F0 generation mouse comprises an XY oocyte.

In one embodiment, the F1 generation progeny mouse comprises a genome completely derived from the donor ES cell.

In one embodiment, the frequency of crosses of F0 generation male and F0 generation female mice that give rise to fully ES cell-derived mice is 100%.

In one aspect, a method for generating a mouse pup litter is provided, comprising introducing XY donor ES cells prepared according to the invention into host mouse embryos, gestating the embryos in a suitable mouse, and obtaining a litter of mouse pups that comprises at least one XY female mouse pup that upon reaching sexual maturity is a fertile XY female mouse.

In one embodiment, the percentage of XY female mouse pups born that upon reaching sexual maturity are fertile is about 10%, 15%, 20%, 25%, 30%, 35%, 40%, 45%, or 50%. In a specific embodiment, the percentage is about 15-25%.

In one aspect, a method for maintaining an XY ES cell in culture is provided, wherein the XY ES cell is maintained under conditions that promote or favor development of a female XY mouse following introduction of the XY ES cell into a host embryo and following gestation in a suitable female mouse. The method comprises maintaining the male ES cell in a suitable culture medium that comprises a base medium and supplements, wherein the base medium exhibits an osmolality of about 240-320 mOsm/kg, a conductivity of about 10-14 mS/cm, an alkaline metal halide salt concentration of about 50-105 mM, a salt of carbonic acid concentration of 10-40 mM, and/or a combined alkaline metal salt and carbonic acid salt concentration of about 80-140 mM. In one embodiment, the XY ES cell is maintained in the medium (with supplements for maintaining ES cells) for a period of 1, 2, 3, 4, 5, or 6 days, or 1 week, 8, 9, 110, 11, or 12 days, 2 weeks, 3 weeks, or 4 weeks prior to introduction into a host embryo. In a specific embodiment, the ES cell is maintained in the medium (low-salt base medium with supplements for maintaining ES cells) for about 2-4 weeks prior to introduction into the host embryo.

In one embodiment, the base medium exhibits an osmolality of no more than about 320, 310, 300, 290, 280, 270, 260, 250, or 240 mOsm/kg. In one embodiment, the base medium exhibits an osmolality of no more than about 240-320, 250-310, or 260-300 mOsm/kg. In a specific embodiment, the base medium exhibits an osmolality of about 270 mOsm/kg.

In one embodiment, the base medium exhibits a conductivity of no more than about 10.0, 10.5, 11.0, 11.5, 12.0, 12.5, 13.0, 13.5, or 14.0 mS/cm. In one embodiment, the base medium exhibits a conductivity of no more than about 10-14 mS/cm or 11-13 mS/cm. In a specific embodiment, the base medium exhibits a conductivity of about 12-13 mS/cm.

In a specific embodiment, the base medium exhibits a conductivity of about 12-13 mS/cm and an osmolality of about 260-300 mOsm/kg. In a further specific embodiment, the base medium comprises sodium chloride at a concentration of about 90 mM NaCl. In a further specific embodiment, the concentration of sodium chloride is about 70-95 mM. In a further specific embodiment, the base medium comprises sodium bicarbonate at a concentration of less than about 35 mM. In a further specific embodiment, the concentration of sodium bicarbonate is about 20-30 mM.

In one embodiment, the base medium exhibits a concentration of a salt of an alkaline metal and a halide of no more than about 100 mM. In one embodiment, the salt of the alkaline metal and the halide is NaCl. In one embodiment, the concentration of the salt of the alkaline metal and halide is no higher than 90, 80, 70, 60, or 50 mM. In one embodiment, the concentration in the base medium of the salt of the alkaline metal and halide is about 60-105, 70-95, or 80-90 mM. In a specific embodiment, the concentration is about 85 mM.

In one embodiment, the base medium exhibits a concentration of a salt of carbonic acid. In one embodiment, the salt of carbonic acid is a sodium salt. In one embodiment, the sodium salt is sodium bicarbonate. In one embodiment, the concentration of carbonic acid salt in the base medium is no higher than 40, 35, 30, 25, or 20 mM. In one embodiment the concentration of carbonic acid salt in the base medium is about 10-40, in another embodiment about 20-30 mM. In a specific embodiment, the concentration is about 25 or 26 mM.

In one embodiment, the sum of the concentration of the salt of the alkaline metal and halide and the salt of carbonic acid in the base medium is no more than 140, 130, 120, 110, 100, 90, or 80 mM. In one embodiment, the sum of the concentration of the salt of the alkaline metal and halide and the salt of carbonic acid in the base medium is about 80-140, 85-130, 90-120, 95-120, or 100-120 mM. In a specific embodiment, the sum of the concentration of the salt of the alkaline metal and halide and the salt of carbonic acid in the base medium is about 115 mM.

In one embodiment, the molar ratio of the salt of the alkaline metal and halide and the salt of carbonic acid is higher than 2.5. In one embodiment, the ratio is about 2.6-4.0, 2.8-3.8, 3-3.6, or 3.2-3.4. In one embodiment, the ratio is 3.3-3.5. In a specific embodiment, the ratio is 3.4.

In one embodiment, the base medium exhibits an osmolality of about 250-310 mOsm/kg, and a concentration of a salt of an alkaline metal and a halide of about 60-105 mM. In a further embodiment, the base medium has a concentration of a salt of carbonic acid of about 20-30 mM. In a further embodiment, the sum of the concentrations of the salt of an alkaline metal and halide and the salt of carbonic acid is about 80-140 mM. In a further embodiment, the conductivity of the base medium is about 12-13 mS/cm.

In one aspect, a method for maintaining a donor XY ES cell in culture is provided, under conditions as described herein, wherein following introduction of the donor XY ES cell into a host embryo to form a chimeric embryo and gestation of the chimeric embryo in a suitable animal, the chimeric embryo develops into a mouse pup that is at least 90% XY and is a female which, upon attaining sexual maturity, is fertile.

In one embodiment, the mouse pup is at least 92%, 94%, 96%, 98%, or 99.8% XY.

In one aspect, a method is provided for making a fertile XY female animal, comprising maintaining an XY donor cell in a medium comprising low-salt base medium prior to introduction of the donor cell into a host embryo, introducing the donor cell into the host embryo, gestating the host embryo in a suitable animal to term, and following gestation obtaining an XY female animal therefrom, wherein upon reaching sexual maturity the XY female animal is fertile.

In one embodiment, the XY donor cell is a mouse ES cell, and the host embryo is an embryo from an XX female mouse.

In one embodiment, the culture in which the donor cell is maintained comprises a base medium as described herein, and one or more supplements suitable for maintaining mouse ES cells in culture. In a specific embodiment, the one or more supplements suitable for maintaining a mouse ES cell in culture are FBS (90 mL FBS/0.5 L base medium), glutamine (2.4 mmoles/0.5 L base medium), sodium pyruvate (0.6 mmoles/0.5 L base medium), nonessential amino acids (<0.1 mmol/0.5 L base medium), 2-mercaptoethanol, LIF, and one or more antibiotics.

In one embodiment, the donor cell is maintained in a medium with a low-salt base medium for at least 1, 2, 3, 4, 5, or 6 days, or 1 week, 8, 9, 110, 11, or 12 days, 2 weeks, 3 weeks, or 4 weeks prior to introducing the donor cell into a host embryo. In a specific embodiment, the donor cell is maintained in a medium with a low-salt base medium at least 2-4 weeks prior to introduction of the donor cell into the host embryo.

In one embodiment, the donor cell is maintained (e.g., frozen) in a medium comprising low-salt base medium, and the donor cell is thawed in and maintained in the medium comprising low-salt base medium for at least 1, 2, 3, or 4 or more days before introducing the donor cell into the host embryo. In a specific embodiment, the donor cell is passaged at least once in a medium comprising low-salt base medium, the cell is frozen in the medium comprising low-salt base medium, and the cell is thawed in a medium comprising low-salt base medium and grown for 1, 2, 3, 4, 5, or 6 days or more, or 1 week, 8, 9, 110, 11, or 12 days, 2 weeks, 3 weeks, 4 weeks, or more prior to introduction into the host embryo.

In one embodiment, the donor cell is maintained for a period of one, two, three, or four days prior to introduction into a host embryo. In on embodiment, the donor cell is maintained in the medium comprising the recited base medium for a period of 3 days.

In one aspect, a method is provided for making a breeding pair of fertile mice, each fully derived from a donor ES cell, in the same F0 generation, comprising: maintaining donor male mouse XY ES cells in culture comprising a base medium and supplements as described herein, wherein the ES cells are maintained in the base medium and supplements for a period of at least one day; introducing the ES cells into host embryos (e.g., from XX mice) to form chimeric embryos; gestating the chimeric embryos in a suitable mouse to term; and, obtaining from the suitable mouse a litter of mouse pups comprising an F0 generation fertile male XY mouse fully derived from a donor ES cell and comprising an F0 generation fertile female XY mouse fully derived from a donor ES cell.

In one embodiment, the donor ES cells comprise a genetic modification. In one embodiment, the donor ES cells comprise a genetic modification that is heterozygous. In one embodiment, the donor ES cells comprise a heterozygous genetic modification, the F0 generation fertile male mouse and the F0 generation fertile female XY mouse are each heterozygous for the genetic modification, and the F0 generation fertile male and the F0 generation fertile female are bred with one another and produce a progeny that is an F1 generation mouse homozygous for the genetic modification.

In one embodiment, the ES cells are maintained for a period of two days, three days, or four days or more.

In one aspect, a method for making a fertile female XY mouse in an F0 generation is provided, comprising the steps of (a) maintaining a donor XY mouse ES cell in a medium comprising a base medium, and supplements suitable for maintaining mouse ES cells in culture, (b) introducing the donor XY mouse ES cell into a host embryo, (c) gestating the host embryo, and (d) obtaining an XY female mouse progeny, wherein upon attaining sexual maturity the XY female mouse is fertile. The base medium according to this aspect exhibits one or more characteristics selected from (1) an osmolality of from 200 mOsm/kg to less than 329 mOsm/kg, (2) a conductivity of about 11-13 mS/cm, (3) a salt of an alkaline metal and a halide in a concentration of about 50-110 mM, (4) a carbonic acid salt concentration of about 17-30 mM, and (5) a total alkaline metal halide salt and carbonic acid salt concentration of about 85-130 mM.

In one embodiment, the donor XY mouse ES cell comprises a genetic modification. In some embodiments, the genetic modification comprises one or more of an endogenous nucleic acid sequence, a substitution of one or more nucleic acids, a replacement of an endogenous nucleic acid sequence with a heterologous nucleic acid sequence, a knockout, and a knock-in. In one particular embodiment, the genetic modification is a knock-out of a STEAP2 gene.

In one embodiment, the base medium contains inter alia (exhibits) 50±5 mM NaCl and 26±5 mM carbonate, with an osmolality of 218±22 mOsm/kg. In a specific embodiment, the base medium exhibits about 3 mg/mL NaCl and 2.2 mg/mL sodium bicarbonate, with an osmolality of about 218 mOsm/kg.

In another embodiment, the base medium exhibits 87±5 mM NaCl and 18±5 mM, with an osmolality of 261±26 mOsm/kg. In a specific embodiment, the base medium exhibits about 5.1 mg/mL NaCl and 1.5 mg/mL sodium bicarbonate, with an osmolality of about 261 mOsm/kg.

In another embodiment, the base medium exhibits 110±5 mM NaCl and 18±5 mM carbonate, with an osmolality of 294±29 mOsm/kg. In a specific embodiment, the base medium exhibits about 6.4 mg/mL NaCl and 1.5 mg/mL sodium bicarbonate, with an osmolality of about 294 mOsm/kg.

In another embodiment, the base medium exhibits 87±5 mM NaCl and 26±5 mM carbonate, with an osmolality of about 270±27 mOsm/kg. In a specific embodiment, the base medium exhibits about 5.1 mg/mL NaCl and 2.2 mg/mL sodium bicarbonate, with an osmolality of about 270 mOsm/kg.

In another embodiment, the base medium exhibits 87±5 mM NaCl, 26±5 mM carbonate, and 86±5 mM glucose, with an osmolality of 322±32 mOsm/kg. In a specific embodiment, the base medium exhibits about 5.1 mg/mL NaCl, about 2.2 mg/mL sodium bicarbonate, and about 15.5 mg/mL glucose, with an osmolality of about 322 mOsm/kg.

In one aspect, a method of producing a transgenic mouse homozygous for a genetic modification in the F1 generation is provided, which comprises the steps of (a) crossing an F0 XY fertile female mouse produced according to the preceding method with a cohort F0 XY male mouse and (b) obtaining a F1 progeny mouse that is heterozygous for the genetic modification. According to this aspect, the F0 XY fertile female mouse and the F0 XY male mouse each is heterozygous for the genetic modification. In some embodiments, the genetic modification comprises one or more of an endogenous nucleic acid sequence, a substitution of one or more nucleic acids, a replacement of an endogenous nucleic acid sequence with a heterologous nucleic acid sequence, a knockout, and a knock-in.

In one specific embodiment, the F0 XY fertile female mouse is made according to the preceding method in which the base medium exhibits 50±5 mM NaCl and 26±5 mM carbonate, with an osmolality of 218±22 mOsm/kg. In a particular embodiment, the base medium exhibits about 3 mg/mL NaCl and 2.2 mg/mL sodium bicarbonate, with an osmolality of about 218 mOsm/kg.

In one aspect, a transgenic mouse homozygous for a genetic modification, which is produced according to the preceding method, is provided.

In one aspect, a fertile female XY mouse produced according to any of the preceding methods is provided. In one embodiment, the ES cells, from which the XY female mouse is derived, were maintained in a base medium that exhibits 50±5 mM NaCl and 26±5 mM carbonate, with an osmolality of 218±22 mOsm/kg. In a specific embodiment, the base medium exhibits about 3 mg/mL NaCl and 2.2 mg/mL sodium bicarbonate, with an osmolality of about 218 mOsm/kg.

Unless expressly stated, or apparent from the context, any aspect or embodiment described herein may be combined with one another.

BRIEF DESCRIPTION OF THE FIGURES

FIG. 1 shows the results of breeding using F0 generation female XY mice made from different XY ES cell clones.

FIG. 2 shows generation of XY female mice from ES cells incubated with low-salt DMEM, DMEM, or low-salt DMEM supplemented with FS (Wnt-3a-conditioned media, i.e., media conditioned by mouse L-cells transfected with a Wnt-3a-expression construct), NaCl and NaHCO$_3$.

DETAILED DESCRIPTION

All publications cited in this disclosure are hereby incorporated by reference.

The phrase "base medium" or "base media" includes a base medium known in the art (e.g., DMEM) that is suitable for use (with added supplements) in growing or maintaining ES cells in culture. Base media suitable for making a fertile XY female (i.e., "low-salt DMEM") differs from base media typically used to maintain ES cells in culture. For purposes of discussing base media in general, base media that are not suitable for making fertile XY females are described in this section as "DMEM" and in the following table (e.g., typical DMEM media). For purposes of discussing base media suitable for making fertile XY females, the phrase "low-salt DMEM" is used. Differences between base media typically used to maintain ES cells in culture (e.g., DMEM) and base media suitable for making fertile XY females (e.g., "low-salt DMEM") are articulated herein. The phrase "low-salt DMEM" is used for convenience; suitable DMEM for making fertile XY females exhibits characteristics not limited to "low-salt," but includes those described herein. For example, the DMEM shown in Table 1 can be made suitable for making fertile XY females by altering the sodium chloride and/or sodium bicarbonate concentrations as provided for herein, which will also result in a different osmolality and a different conductivity as compared with the DMEM shown in Table 1. An example of base medium is Dulbeco's Modified Eagle's Medium (DMEM), in various forms (e.g., Invitrogen DMEM, Cat. No. 11971-025) (Table 1). A suitable low-salt DMEM is available commercially as KO-DMEM™ (Invitrogen Cat. No. 10829-018). Base medium is typically supplemented with a number of supplements known in the art when used to maintain cells in culture for use as donor cells. Such supplements are indicated as "supplements" or "+supplements" in this disclosure.

TABLE 1

DMEM Base Media for Maintaining ES Cells

| Component | mg/L | mM |
|---|---|---|
| Glycine | 30 | 0.4 |
| L-Arginine•HCl | 84 | 0.398 |
| L-Cystine•2HCl | 63 | 0.201 |
| L-Glutamine | 584 | 4 |
| L-Histidine•HCl•H$_2$O | 42 | 0.2 |
| L-Isoleucine | 105 | 0.802 |
| L-Leucine | 105 | 0.802 |
| L-Lysine•HCl | 146 | 0.798 |
| L-Methionine | 30 | 0.201 |
| L-Phenylalanine | 66 | 0.4 |
| L-Serine | 42 | 0.4 |
| L-Threonine | 95 | 0.798 |
| L-Tryptophan | 16 | 0.0784 |
| L-Tyrosine disodium salt dihydrate | 104 | 0.398 |
| L-Valine | 94 | 0.803 |
| Choline chloride | 4 | 0.0286 |
| D-Calcium pantothenate | 4 | $8.39 \times 10^{-3}$ |
| Folic Acid | 4 | $9.07 \times 10^{-3}$ |
| Niacinamide | 4 | 0.0328 |
| Pyridoxine•HCl | 4 | 0.0196 |
| Riboflavin | 0.4 | $1.06 \times 10^{-3}$ |
| Thiamine•HCl | 4 | 0.0119 |
| i-Inositol | 7.2 | 0.04 |
| Calcium Chloride (CaCl$_2$) (anhydrous) | 200 | 1.8 |
| Ferric Nitrate (Fe(NO$_3$)$_3$•9H$_2$O) | 0.1 | $2.48 \times 10^{-4}$ |
| Magnesium Sulfate (MgSO$_4$) (anhyd.) | 97.67 | 0.814 |
| Potassium Chloride (KCl) | 400 | 5.33 |
| D-Glucose (Dextrose) | 4500 | 25 |
| Phenol Red | 15 | 0.0399 |
| NaCl/NaHCO$_3$ Content of DMEM | | |
| Sodium Bicarbonate (NaHCO$_3$) | 3700 | 44.05 |
| Sodium Chloride (NaCl) | 6400 | 110.34 |
| NaCl/NaHCO$_3$ Content of Low-salt DMEM | | |
| Sodium Bicarbonate (NaHCO$_3$) | <3700 | <44.05 |
| Sodium Chloride (NaCl) | <6400 | <110.34 |

The term "supplements" or the phrase "+supplements," includes elements added to base medium for growing or maintaining donor cells in culture, e.g., for maintaining pluripotency or totipotency of donor cells in culture. For example, media supplements suitable for growing or maintaining non-human ES cells in culture include fetal bovine serum (FBS), glutamine, penicillin and streptomycin (e.g., penstrep), pyruvate salts (e.g., sodium pyruvate), nonessential amino acids (e.g., MEM NEAA), 2-mercaptoethanol, and LIF.

In various embodiments of media for maintaining nonhuman donor cells in culture, to about 500 mL of base medium the following supplements are added: about 90 mL FBS (e.g., Hylcone FBS Cat. No. SH30070.03), about 2.4 millimoles of glutamine (e.g., about 12 mL of a 200 mM glutamine solution, e.g., Invitrogen Cat. No. 25030-081), penicillin:streptomycin (e.g., 60,000 units of Penicillin G sodium and 60 mg of streptomycin sulfate, with about 51 mg of NaCl; e.g., about 6 mL of Invitrogen pennstrep, Cat. No. 15140-122), about 0.6 millimoles of sodium pyruvate (e.g., 6 mL of 100 mM sodium pyruvate, Invitrogen Cat. No. 11360-070), about 0.06 millimoles of nonessential amino acids (e.g., about 6 mL of MEM NEAA, e.g., MEM NEAA from Invitrogen Cat. No. 11140-050), about 1.2 mL 2-mercaptoethanol, and about 1.2 micrograms of LIF (e.g., about 120 microliters of a 10$^6$ units/mL LIF preparation; e.g., about 120 microliters of Millipore ESGRO™-LIF, Cat. No. ESG1107). When composing base media for maintaining XY ES cells for making fertile XY females, typically the same supplements in about the same amounts are employed, but the composition of the base medium will differ (from DMEM, e.g., from the medium described in the table above) and the difference(s) correspond to the difference(s) taught herein.

In some embodiments, supplements include Wnt-conditioned media, e.g., Wnt-3a conditioned media.

The term "animal," in reference to donor cells and/or host embryos, includes mammals, fishes, and birds. Mammals include, e.g., humans, non-human primates, rodents (e.g., mice, rats, hamsters, guinea pigs), livestock (e.g., bovine species, e.g., cows, steer, etc.; ovine species, e.g., sheep, goats, etc.; and porcine species, e.g., pigs and boars). Birds include, e.g., chickens, turkeys, ostrich, geese, ducks, etc. The phrase "non-human animal," in reference to donor cells and/or host embryos, excludes humans.

In various embodiments, the donor cell and/or the host embryo are not from one or more of the following: *Akodon* spp., *Myopus* spp., *Microtus* spp., *Talpa* spp. In various embodiments, the donor cell and/or the host embryo are not from any species of which a normal wild-type characteristic is XY female fertility. In various embodiments, where a genetic modification is present in the donor cell or the host embryo, the genetic modification is not an XYY or XXY, a Tdy-negative sex reversal, Tdy-positive sex reversal, an X0 modification, an aneuploidy, an SRY translocation or modification, an fgf9$^{-/-}$ genotype, or a SOX9 modification.

Overview

Methods for making nonhuman animals, e.g., mice, from donor ES cells and host embryos are known in the art. Donor ES cells are selected for certain characteristics that enhance the ability of the cells to populate a host embryo and thus contribute in part or in substantial part to an animal formed by the donor ES cells and the host embryo. The animal formed may be male or female, based in large part on the genotype of the ES cell (e.g., XY or XX).

The majority of ES cell liens for making mice have a male XY genotype. Because of the dominance of the Y chromosome in mammalian sex determination, XY ES cells, when introduced into a host embryo and gestated, nearly always result in the first generation (F0) in phenotypically male animals that are chimeras, i.e., that contain cells derived from the male donor ES cell (XY) and cells derived from the host embryo, which can be either male (XY) or female (XX). To the extent that phenotypic females are observed in the F0 generation, these typically arise from the introduction of XY ES cells into a female XX embryo that results in a chimera whose ES cell contribution is insufficient to masculinize the embryonic genital ridge. In most cases such female chimeras do not produce oocytes derived from the XY ES cells and, therefore, are not capable of transmitting the ES cell genome to the next generation. In rare cases, female chimeras do not produce oocytes derived from the XY ES cells; these females can transmit the ES cell genome to the next generation (see, e.g., Bronson et al. (1995) High incidence of XXY and XYY males among the offspring of female chimeras from embryonic stem cells, Proc. Natl. Acad. Sci USA 92:3120-3123).

Phenotypically female mice with an XY genotype can arise as the result specific mutations. See, e.g., Lovell-Badge et al. (1990) XY female mice resulting from a heritable mutation in the primary testis determining gene, Tdy, Development 109: 635-646; see also, Colvin et al. (2001) Male-to-Female Sex Reversal in Mice Lacking Fibroblast Growth Factor 9, Cell 104(6):875-889 (Fgf–/– XY females that die at birth from lung hypoplasia). The South American Akadon spp. of rodents comprise XY females (see, e.g., Hoekstra et al. (2000) Multiple origins of XY female mice (genus *Akodon*): phylogenetic and chromosomal evidence, Proc. R. Soc. Lond. B 267:1825-1831), but ES cell lines from such mice are generally not available and not widely used, if at all.

In some instances, e.g., using the VELOCIMOUSE® method (see, e.g., U.S. Pat. Nos. 7,659,442, 7,576,259, 7,294,754, and Poueymirou et al. (2007) F0 generation mice fully derived from gene-targeted embryonic stem cells allowing immediate phenotypic analyses, Nat. Biotech. 25(1):91-99; each hereby incorporated by reference), it is possible to obtain F0 generation mice that are fully derived from the donor ES cell. Under normal circumstances and standard experimental conditions, XY donor ES cells produce only phenotypically male fully ES cell-derived mice, while ES cells thar are XX or X) (XY ES cells that have lost the Y chromosome) produce only phenotypically female fully ES cell-derived mice. To produce mice with homozygous targeted mutations from the male and female fully ES celll-derived mice requires two subsequent generations of breeding to first produce the F1 generation heterozygous male and females that when intercrossed have the potential to produce homozygous progeny in the F2 generation.

The inventors have devised a method for making a phenotypically female fertile XY mouse from an XY donor cell (e.g., an XY donor cell derived from a phenotypically male mouse) and a suitable host embryo. The method comprises making such a mouse in the F0 generation, which allows for forming a breeding pair (a male F0 and a female F0) in the F0 generation. This is particularly useful where the donor cell comprises a heterozygous genetic modification, and a homozygous mouse is desired. Although this disclosure illustrates the invention in the context of making phenotypically female fertile XY mice from donor mouse XY ES cells, the methods and compositions described herein may be applied to make phenotypically female XY fertile nonhuman animals from any suitable nonhuman cell (e.g., an iPS cell, an ES cell, or a pluripotent cell) and any suitable nonhuman embryo.

Methods and compositions are described that include conditions for maintaining a donor cell such that when the donor cell is used to generate an animal by introducing the donor cell into a host embryo, the animal so generated includes a phenotypically female fertile XY animal. A phenotypically female fertile XY animal includes an animal that exhibits sufficient phenotypically female characteristics to ovulate and to gestate an embryo upon fertilization of an ovum produced by ovulation in the animal, including to gestate an embryo to term and give birth to a live-born animal.

The inventors have devised a method that results, in various embodiments at least about 10%, 15%, 20%, or 25% or more of the time, in birth of a fertile female XY mouse from an XY mouse ES cell.

Animal Husbandry

In one aspect, a method is provided for generating a female animal from a sperm cell and an egg cell, comprising maintaining the sperm cell and/or the egg cell in a medium comprising low-salt base medium for one, two, three, or four or more days prior to fertilization, contacting the sperm cell and the egg cell under conditions that permit fertilization to form a fertilized egg, implanting the fertilized egg in a suitable host for gestation, gestating in the host, and obtaining a litter comprising a female animal.

In one embodiment, the fertilized egg is further maintained in the medium comprising low-salt base medium for one, two, three, or four or more days prior to implantation in the suitable host.

In one aspect, a method is provided for favoring the generation of a female animal from a fertilized egg or an embryo, comprising maintaining the fertilized egg or embryo in a medium comprising low-salt base medium for one, two, three, or four or more days prior to implantation in a suitable host, implanting the fertilized egg or embryo into a suitable host for gestation, gestating the fertilized egg or embryo in the host, and obtaining a litter comprising a female animal.

In one aspect, the methods and compositions of the invention are employed to make a female pet, a female domesticated farm animal, a female animal as a scientific research subject, or an animal of an endangered species. In one embodiment, the animal is a mouse, rat, hamster, monkey, ape, cat, dog, cow, horse, bull, sheep, goat, pig, deer, and bison.

EXAMPLES

Example 1

Donor XY ES Cells and Host Embryos

Donor Cells and Host Embryos.

Donor ES cells were 129S6C57B16/F1 hybrid ES cells. The donor ES cells were frozen in freezing medium containing 10% DMSO until use. Once thawed, donor ES cells were maintained in base medium and supplements as described below. Host embryos were from Swiss Webster (SW) mice, and were maintained in KSOM medium (Millipore) until use. Eight-cell embryos were obtained as previously described (Poueymirou et al. (2007) Nature Biotech. 25(1):91-99; U.S. Pat. Nos. 7,659,442, 7,576,259, and 7,294,754).

DMEM ES cells: ES cells prepared and frozen in DMEM were thawed in DMEM, grown for three days, and microinjected into host embryos in DMEM.

Low-salt DMEM ES cells: ES cells prepared and frozen in low-salt DMEM were thawed in low-salt DMEM (KO-DMEM), grown for three days, and microinjected into host embryos in DMEM.

FS low-salt DMEM: ES cells prepared and frozen in low-salt DMEM were thawed and maintained in low-salt DMEM (440 mL)+10% Wnt-3a-conditioned media (FS) (60 mL), and microinjected into host embryos in DMEM.

Low-salt DMEM+NaCl+NaHCO$_3$: ES cells prepared and frozen in low-salt DMEM with added NaCl (1,300 mg/L) and NaHCO$_3$ (1,500 mg/L) and microinjected into host embryos in DMEM.

10% Wnt-3a-conditioned media (FS): Wnt-3a-conditioned media was made from cultures of mouse L cells transformed with a Wnt-3a expression vector (ATCC CRL-2647). The L cells are grown according to ATCC instructions (except that KO-DMEM™ is used in place of DMEM), in a FibraStage™ (New Brunswick) system.

Example 2

Making F0 Generation Mice Derived from Donor ES Cells

Generating F0 Generation Mice.

Donor ES cells were introduced into 8-cell stage pre-morula host embryos using the VELOCIMOUSE® method, as described previously (Poueymirou et al. (2007) Nature Biotech. 25(1):91-99; U.S. Pat. Nos. 7,659,442, 7,576,259, and 7,294,754), except that the mouse ES cells were maintained in the base medium plus supplements as described herein. For microinjection, ES cells were grown and microinjected into the embryos, and the embryos were cultured overnight in either KSOM or DMEM medium prior to implantation into surrogate mothers.

Example 3

F0 Generation Fertile Female Mice from Donor XY ES Cells

In a typical protocol, ES cells are thawed in the presence of KO-DMEM™ and grown for one passage (about 5 five days). Passaged cells are then electroporated with a gene targeting vector and then placed under selection for 10 days in a medium comprising KO-DMEM™ (Invitrogen Cat. No. 10829-018). Drug-resistant cells are harvested and expanded in a medium comprising KO-DMEM™, then frozen. For microinjection, cells are thawed in KO-DMEM™ and grown for 3 days in KO-DMEM™, then microinjected into embryos in DMEM. The embryos are then introduced into surrogate mothers for gestation.

Mouse pups were initially characterized as male or female based on the appearance of external genitalia in order to select breeding pairs.

FIG. 1 shows that F0 XY females exhibit a high rate of fertility. Twenty-one out of 33 F0 XY females produced litters.

Example 4

Comparing DMEM with Low-Salt DMEM

Osmolality was measured on a Advanced® Model 3250 Single-Sample Osmometer. Conductivity was measured on a Mettler Toledo GmbH SevenMulti™ ECN #15055 conductivity meter.

The effect of low-salt DMEM and of DMEM (each with supplements) on the formation of F0 generation XY females from XY ES cells was studied. Table 2 shows the osmolality and conductivity values of base media with and without additional salts and/or supplements. The indicator "+supplements"=addition (to 0.5 L of base medium) of the following: 90 mL Hyclone FBS (Cat. No. SH30070.03), 12 mL of Invitrogen glutamine solution (Cat. No. 25030-081), 6 mL of Invitrogen Pen Strep (Cat. No. 15140-122), 6 mL of Invitrogen sodium pyruvate (Cat. No. 11360-070), 6 mL of MEM NEAA (Invitrogen Cat. No. 11140-050), 1.2 mL 2-mercaptoethanol, and 120 microliters of Millipore ESGRO™-LIF (Cat. No. ESG1107).

FIG. 2 shows a comparison of XY ES cells grown in different media prior to microinjections into host embryos. XY ES cells grown and maintained in low-salt DMEM and then injected into embryos produced XY females. XY ES cells grown and maintained in low-salt DMEM supplemented with NaCl and NaHCO$_3$ and then injected into embryos produced no XY females. This demonstrates that XY female production is promoted when XY ES cells are maintained in low-salt DMEM, and that the sex ratio of XY ES cells can be controlled by altering the salt concentration of the base medium. Adding a Wnt-3a-conditioned medium (10% FS) to a low-salt DMEM increased the frequency of production of F0 XY females.

Furthermore, the efficiency of generating ES cell-derived mice in the F0 increased when the ES cells were maintained in Low-salt DMEM. The ratio of ES cell-derived pups to total pups generated in the F0 generation increased from about 23% for ES cells maintained in DMEM, to 61% for ES cells maintained in low-salt DMEM, to 72% for ES cells maintained in low-salt DMEM supplemented with 10% Wnt-3a-conditioned media. See FIG. 2.

TABLE 2

Comparison of DMEM and Low-salt DMEM Physical Characteristics

| Medium for ES Cells | Conductivity (mS/cm) | Osmolality (mOsm/kg) |
|---|---|---|
| Low-salt DMEM, alone | 12.84 | 270 |
| DMEM, alone | 15.40 | 337 |
| Low-salt DMEM + NaHCO$_3$ + NaCl, alone | 15.82 | 342 |
| Low-salt DMEM, + supplements | 12.75 | 279 |
| DMEM, + supplements | 14.91 | 330 |
| Low-salt DMEM + NaHCO$_3$ + NaCl, + supplements | 15.29 | 335 |

Example 5

Analysis of F0 Generation Mice

Coat Color.

Mice were analyzed for coat color contribution from donor XY ES cells (agouti) and host embryo (white). None of the F0 generation mice exhibited any coat color contribution from host embryos.

Gender.

F0 generation pups were identified as female or male by visual inspection of the external genitalia. F0 pups were assigned gender and paired for breeding based on visual inspection.

Genotyping.

The presence of an X chromosome was detected using a TAQMAN™ QPCR assay specific for a sequence on the X chromosome. The presence of Y chromosome was detected using a TAQMAN™ QPCR assay specific for a sequence on the Y chromosome. The genotyping of phenotypically female F0 generation mice indicated a single copy of the X chromosome and a single copy of the Y chromosome in those phenotypically female mice tested.

Karyotyping.

Six F0 generation XY females were karyotyped. Karyotyping results indicated that all six had a normal X and a normal Y chromosome.

XY Female Reproductive Anatomy.

Several F0 generation XY females were examined for internal reproductive organs. All of the F0 XY females examined appeared to have normal female internal reproductive organs. Tissue samples from each reproductive organ (ovary, oviduct, uterus) were genotyped, and the results indicated that the tissues had a uniform XY genotype.

Example 6

Analysis of the Effect of Osmolality on Efficiency of Generating ES Cell-Derived Pups and XY Females To determine the effect of osmolality on the generation of XY females from XY ES cells maintained in low-salt, low-carbonate DMEM, glucose was added to low-salt, low-carbonate DMEM to bring the osmolality to within that of DMEM. Osmolality was measured on a Advanced® Model 3250 Single-Sample Osmometer.

Donor XY ES cells were maintained in low-salt, low-carbonate, high glucose DMEM containing inter alia 5.1 mg/ml NaCl, 2.2 mg/ml NaHCO$_3$, and 15.5 mg/ml glucose, having an osmolality of 322 mOsm/kg ("DMEM-LS/LC/

HG"). Upon transfer of said ES cells into embryos per the VELOCIMOUSE® method (supra), 15% of all resultant ES cell-derived F0 progeny were phenotypically female XY mice. As a negative control, in the F0 generation, no phenotypically female XY mice were derived from ES cells maintained in DMEM ("DMEM":6.4 mg/ml NaCl, 3.7 mg/ml NaHCO$_3$, and 4.5 mg/ml glucose; 329 mOsm/kg). This 15% F0 XY female result lies between the 0% F0 XY females from DMEM-derived ES cells (329 mOsm/L) and the 27.8% F0 XY female mice derived from ES cells maintained in low-salt, low carbonate DMEM ("DMEM-LS/LC": 5.1 mg/ml NaCl, 2.2 mg/ml NaHCO$_3$, and 4.5 mg/ml glucose; 270 mOsm/kg). Thus, one interpretation is that osmolality provides some of the feminization effect, but not all. An alternative explanation is that the low salt and/or low carbonate provides the feminization effect, and high glucose impedes to some extent the feminization of XY ES cells. See Table 3.

Furthermore, the efficiency of generating ES cell-derived mice (Table 3) in F0 when the ES cells were maintained in DMEM-LS/LC/HG (i.e., about 40%) was greater than that for ES cells maintained in DMEM (i.e., about 22%), but not quite as high as that for ES cells maintained in DMEM-LS/LC (i.e., about 51%). See Table 3.

These results confirm that low salt and/or low carbonate contribute both to the increase in proportion of ES cell-derived F0 progeny as well as F0 XY females. (See Table 3.)

Example 8

Analysis of the Effect of Carbonate Concentration on Efficiency of Generating ES Cell-Derived Pups and XY Females To determine the effect of carbonate concentration on the generation of XY females from XY ES cells, ES cells were maintained in low salt and very low carbonate media (DMEM-LS/VLC: 5.1 mg/mL NaCl, 1.5 mg/mL NaHCO3, 4.5 mg/mL glucose, at 261 mOsm/kg). Upon transfer of said ES cells into embryos per the VELOCIMOUSE® method (supra), 34% of all resultant ES cell-derived F0 progeny were phenotypically female XY mice; a slight increase over the DMEM-LS/LC control level of 27.8%. Interestingly, 87.7% of the F0 pups resulting from the transfer of ES cells maintained in DMEM-LS/VLC media were ES cell-derived; whereas only 50.7% and 22.4% were ES cell-derived in the DMEM-LS/LC and DMEM controls, respectively.

TABLE 3

Effect of Osmolarity, Salt, and Carbonate on ES-cell Derived Pups and F0 XY Females

| Media | Osmolality (mOsm/kg) | NaCl (mg/mL) | NaHCO$_3$ (mg/mL) | Glucose (mg/mL) | ES-Derived pups/Total pups | ES-derived pups XY male | ES-derived pups XY female |
|---|---|---|---|---|---|---|---|
| DMEM | 329 | 6.4 | 3.7 | 4.5 | 13/58 (22.4%) | 13/13 | 0/13 (0%) |
| DMEM-LS/LC | 270 | 5.1 | 2.2 | 4.5 | 36/71 (50.7%) | 26/36 | 10/36 (27.8%) |
| DMEM-LS/LC/HG | 322 | 5.1 | 2.2 | 15.5 | 20/50 (40%) | 17/20 | 3/20 (15%) |
| DMEM-VLS/LC | 218 | 3.0 | 2.2 | 4.5 | 53/58 (91.4%) | 35/53 | 18/53 (34.0%) |
| DMEM-LS/VLC | 261 | 5.1 | 1.5 | 4.5 | 50/57 (87.7%) | 33/50 | 17/50 (34%) |
| DMEM-VLC | 294 | 6.4 | 1.5 | 4.5 | 49/68 (72.1%) | 35/49 | 14/49 (28.6%) |

Example 7

Analysis of the Effect of Salt Concentration on Efficiency of Generating ES Cell-Derived Pups and XY Females To determine the effect of salt concentration or ionic strength on the generation of XY females from XY ES cells, ES cells were maintained in very low salt (DMEM-VLS/LC: 3.0 mg/mL NaCl, 2.2 mg/mL NaHCO3, 4.5 mg/mL glucose, at 218 mOsm/kg). Upon transfer of said ES cells into embryos per the VELOCIMOUSE® method (supra), 34% of all resultant ES cell-derived F0 progeny were phenotypically female XY mice; a slight increase over the DMEM-LS/LC control level of 27.8%. Interestingly, 91.4% of the F0 pups resulting from the transfer of ES cells maintained in DMEM-VLS/LC media were ES cell-derived; whereas only 50.7% and 22.4% were ES cell-derived in the DMEM-LS/LC and DMEM controls, respectively.

In another experiment, ES cells were maintained in high salt and low carbonate media (DMEM-HS/VLC: 6.4 mg/mL NaCl, 1.5 mg/mL NaHCO3, 4.5 mg/mL glucose, at 294 mOsm/kg). Upon transfer of said ES cells into embryos per the VELOCIMOUSE® method (supra), 28.6% of all resultant ES cell-derived F0 progeny were phenotypically female XY mice; a slight increase over the DMEM-LS/LC control level of 27.8%. Interestingly, 72.1% of the F0 pups resulting from the transfer of ES cells maintained in DMEM-HS/VLC media were ES cell-derived; whereas only 50.7% and 22.4% were ES cell-derived in the DMEM-LS/LC and DMEM controls, respectively.

These results confirm that low carbonate contributes both to the increase in proportion of ES cell-derived F0 progeny as well as F0 XY females. (See Table 3.)

Example 9

Phenotype of F0 XY Female Mice

F0 XY phenotypic female mice exhibited relatively normal phenotype attributes compared to F1 XX phenotypic female mice of the same strain. The XY female mice however did exhibit a larger range of values for each physical parameter. The body weight of the adult XY females ranged from about 15 grams to about 30 grams with an average of about 21.5 grams. The body weight of the adult XX females ranged from about 16 grams to about 17 grams with an average of about 16.8 grams.

The ratio of the distance between the anus and the genitals was determined and calculated as a ratio of body mass (anogenital distance (cm)/body mass (g)). The ratio for F0 XY females ranged from about 0.11 cm/g to about 0.24 cm/g with an average of about 0.16 cm/g. The ratio for F1 XX females ranged from about 0.17 cm/g to about 0.19 cm/g with an average of about 0.18 cm/g.

There was no significant difference between the relative masses of various organs (e.g., liver, kidneys, heart and lung, and spleen) for the XY female mice and the XX female mice. Relative masses are expressed as organ mass (mg)/body mass (g). The relative mass of the liver of the F0 XO females ranged from about 35 mg/g to about 50 mg/g with an average of about 42 mg/g. The relative mass of the liver of the F1 XX females ranged from about 37.5 mg/g to about 46.9 mg/g with an average of about 42.5 mg/g. The relative mass of the kidneys of the F0 XO females ranged from about 11.5 mg/g to about 15 mg/g with an average of about 13.4 mg/g. The relative mass of the kidneys of the F1 XX females ranged from about 12.6 mg/g to about 13.8 mg/g with an average of about 13.7 mg/g. The relative combined mass of the heart and lungs of the F0 XO females ranged from about 14.3 mg/g to about 18.9 mg/g with an average of about 16.1 mg/g. The relative combined mass of the heart and lungs of the F1 XX females ranged from about 14.7 mg/g to about 16.1 mg/g with an average of about 15.9 mg/g. The relative mass of the spleen of the F0 XO females ranged from about 2.7 mg/g to about 6.6 mg/g with an average of about 3.3 mg/g. The relative mass of the spleen of the F1 XX females ranged from about 2.7 mg/g to about 4.0 mg/g with an average of about 3.8 mg/g.

The F0 XY female mice were shown to have relatively normal serum levels of electrolytes, enzymes, glucose, proteins, lipids and other indicia compared to syngeneic F1 XX females. The XY female mice however did exhibit a larger range of values for each mearsured serum parameter. The serum sodium levels of the adult XY females ranged from about 150 mEq/L to about 159 mEq/L; and the levels for the XX females ranged from about 148 mEq/L to about 155 mEq/L.

The serum potassium levels of the adult XY females ranged from about 0.7 mEq/L to about 7 mEq/L; and the levels for the XX females were about 0.7 mEq/L.

The serum chloride levels of the adult XY females ranged from about 111 mEq/L to about 121 mEq/L; and the levels for the XX females ranged from about 113 mEq/L to about 120 mEq/L.

The serum calcium levels of the adult XY females ranged from about 7 mEq/L to about 9 mEq/L; and the levels for the XX females were about 7 mEq/L.

The serum alkaline phosphatase levels of the adult XY females ranged from about 124 U/L to about 285 U/L; and the levels for the XX females ranged from about 191 U/L to about 236 U/L.

The serum alanine aminotransferase levels of the adult XY females ranged from about 21 U/L to about 285 U/L; and the levels for the XX females ranged from about 13 U/L to about 34 U/L.

The serum aspartate aminotransferase levels of the adult XY females ranged from about 42 U/L to about 190 U/L; and the levels for the XX females ranged from about 42 U/L to about 269 U/L.

The serum lipase levels of the adult XY females ranged from about 16 U/L to about 49 U/L; and the levels for the XX females ranged from about 21 U/L to about 26 U/L.

The serum glucose levels of the adult XY females ranged from about 227 mg/dL to about 319 mg/dL; and the levels for the XX females ranged from about 255 mg/dL to about 270 mg/dL.

The total serum protein levels of the adult XY females ranged from about 4.6 mg/dL to about 5.2 mg/dL; and the levels for the XX females ranged from about 4.6 mg/dL to about 4.8 mg/dL.

The serum albumin levels of the adult XY females ranged from about 3 mg/dL to about 3.5 mg/dL; and the levels for the XX females ranged from about 3.1 mg/dL to about 3.2 mg/dL.

The serum cholesterol (total) levels of the adult XY females ranged from about 58 mg/dL to about 108 mg/dL; and the levels for the XX females ranged from about 61 mg/dL to about 85 mg/dL.

The serum triglyceride levels of the adult XY females ranged from about 42 mg/dL to about 89 mg/dL; and the levels for the XX females ranged from about 39 mg/dL to about 48 mg/dL.

The serum HDL levels of the adult XY females ranged from about 29 mg/dL to about 57 mg/dL; and the levels for the XX females ranged from about 23 mg/dL to about 42 mg/dL.

The serum LDL levels of the adult XY females ranged from about 3.7 mg/dL to about 11 mg/dL; and the levels for the XX females ranged from about 3.7 mg/dL to about 13 mg/dL.

The blood urea nitrogen (BUN) levels of the adult XY females ranged from about 12 mg/dL to about 27 mg/dL; and the levels for the XX females ranged from about 18 mg/dL to about 21 mg/dL.

The serum magnesium levels of the adult XY females ranged from about 1.6 mg/dL to about 3.2 mg/dL; and the levels for the XX females were about 2.1 mg/dL.

The serum inorganic phosphate levels of the adult XY females ranged from about 5.1 mg/dL to about 10 mg/dL; and the levels for the XX females ranged from about 7.2 mg/dL to about 8.4 mg/dL.

The serum uric acid levels of the adult XY females ranged from about 0.9 mg/dL to about 3.5 mg/dL; and the levels for the XX females ranged from about 0.7 mg/dL to about 2.2 mg/dL.

Example 10

Production of Homozygous Genetically Modified Mouse in the F1 Generation

To determine whether F1 mice homozygous for a genetic modification could be made, F0 XY female mice containing at least one knocked-out allele of a STEAP2 gene was mated to XY male cohort containing the same STEAP2 gene knockout. (The STEAP2 (Six transmembrane epithelial antigen of the prostate 2) gene encodes for a putative 6 membrane metalloreductase with ferrireductase and cupric reductase activity, and has been shown to stimulate the cellular uptake of both iron and copper in vitro. As a cell-surface antigen, STEAP2 is a potential diagnostic or therapeutic target in prostate cancer. STEAP2 was significantly elevated in both untreated primary and hormone-refractory prostate carcinomas than in benign prostate hyperplasias, suggesting that it may be involved in the development of prostate cancer. STEAP2 KO mouse has not been reported. See Ohgami et al., BLOOD, vol. 108(4):1388-1394, 2006.) The results are depicted in Table 4.

TABLE 4

Genotypes of STEAP2 F1 Cohorts from F0 XY Males x F0 XY Females

| Sex Phenotype | Sex Chromosomes (N/%) | | STEAP2 Genotype (N/%) | | |
|---|---|---|---|---|---|
| | | | Wt/wt | Wt/KO | KO/KO |
| Female | XX | (7/15%) | 2/4.3% | 3/6.4% | 2/4.3% |
| | XO | (4/8.5%) | 1/2.1% | 1/2.1% | 2/4.3% |
| | XY | (0/0%) | 0/0% | 0/0% | 0/0% |
| Male | XY | (17/36%) | 6/12.8% | 6/12.8% | 5/10.6% |
| | XXY | (8/17%) | 3/6.4% | 3/6.4% | 2/4.3% |
| | XYY | (11/23.5%) | 3/6.4% | 3/6.4% | 5/10.6% |

We claim:

1. A method for making and breeding a fertile female XY mouse in an F0 generation, comprising:
    (a) maintaining a donor XY mouse ES cell in a medium comprising:
        (i) a base medium; and
        (ii) supplements suitable for growing the mouse ES cells in culture and maintaining pluripotency,
        wherein the donor XY mouse ES cell does not comprise a Tdy-negative sex reversal genetic modification, and wherein the base medium comprises sodium bicarbonate in a concentration of about 1.5-2.2 mg/mL, sodium chloride in a concentration of about 3.0-6.4 mg/mL, and has an osmolality of about 218-322 mOsm/kg;
    (b) introducing a donor XY mouse ES cell from step (a) into a pre-morula stage host mouse embryo;
    (c) introducing the host mouse embryo of step (b) into a recipient female mouse and gestating the host mouse embryo;
    (d) obtaining an F0 XY mouse progeny comprising an F0 XY phenotypically female mouse, wherein upon attaining sexual maturity the F0 XY female mouse is fertile; and
    (e) breeding the F0 XY fertile female mouse to produce progeny.

2. The method of claim 1, wherein the base medium comprises about 3 mg/mL sodium chloride and about 2.2 mg/mL sodium bicarbonate and has an osmolality of about 218 mOsm/kg.

3. The method of claim 2, wherein the base medium further comprises about 4.5 mg/mL glucose.

4. The method of claim 1, wherein the base medium comprises about 5.1 mg/mL sodium chloride and about 1.5 mg/mL sodium bicarbonate and has an osmolality of about 261 mOsm/kg.

5. The method of claim 1, wherein the base medium comprises about 6.4 mg/mL sodium chloride and about 1.5 mg/mL sodium bicarbonate and has an osmolality of about 294 mOsm/kg.

6. The method of claim 1, wherein the base medium comprises about 5.1 mg/mL sodium chloride and about 2.2 mg/mL sodium bicarbonate and has an osmolality of about 270 mOsm/kg.

7. The method of claim 1, wherein the base medium comprises about 5.1 mg/mL sodium chloride, about 2.2 mg/mL sodium bicarbonate, and about 15.5 mg/mL glucose and has an osmolality of about 322 mOsm/kg.

8. The method of claim 1, wherein the donor XY mouse ES cell comprises a genetic modification.

9. The method of claim 1, wherein the maintaining the donor XY mouse ES cell in step (a) further comprises genetically modifying the donor XY mouse ES cell.

10. The method of claim 8, wherein the genetic modification comprises one or more of a deletion in whole or in part of an endogenous nucleic acid sequence, a substitution of one or more nucleic acids, a replacement of an endogenous nucleic acid sequence with a heterologous nucleic acid sequence, a knockout, and a knock-in.

11. The method of claim 8, wherein the genetic modification is a knockout of a STEAP2 gene.

12. The method of claim 8, wherein the genetic modification is a deletion in whole or in part of an endogenous nucleic acid sequence.

13. The method of claim 8, wherein the genetic modification is a substitution of one or more nucleic acids.

14. The method of claim 8, wherein the genetic modification is replacement of an endogenous nucleic acid sequence with a heterologous nucleic acid sequence.

15. The method of claim 8, wherein the genetic modification is a knockout.

16. The method of claim 8, wherein the genetic modification is a knock-in.

17. The method of claim 8, wherein the donor XY mouse ES cell is heterozygous for the genetic modification.

18. The method of claim 1, wherein at least 34% of the F0 XY mouse progeny derived from the donor XY mouse ES cell are phenotypically female XY mice.

19. The method of claim 1, wherein at least 15% of the F0 XY mouse progeny derived from the donor XY mouse ES cell are phenotypically female XY mice.

20. The method of claim 1, wherein all of the females derived from the donor XY mouse ES cell in the F0 generation have a XY genotype.

21. The method of claim 1, wherein the breeding comprises crossing the F0 XY fertile female mouse with a cohort F0 XY male mouse, wherein the F0 XY fertile female mouse and the F0 XY male mouse each is heterozygous for a genetic modification, and obtaining an F1 progeny mouse that is homozygous for the genetic modification.

* * * * *